United States Patent [19]

Minachev et al.

[11] 4,038,335

[45] July 26, 1977

[54] METHOD OF PREPARING BENZENE AND METHYLBENZENES

[76] Inventors: Khabib Minachevich Minachev, Leninsky prospekt, 57, kv. 15; Evgeny Sergeevich Mortikov, Leninsky prospekt, 61/1, kv. 34; Boris Mikhailovich Kozlov, Cherepovetskaya 22, kv. 22, all of Moscow; Alexandr Semenovich Leontiev, ulitsa Gagarina, 13, kv. 13, Bashkirskaya ASSR, Salavat; Nikolai Fedorovich Kononov, ulitsa Garibaldi 13/54, korpus 2, kv. 41, Moscow; Sergei Markovich Lakiza, ulitsa Kolkhoznaya, 5, kv. 12, Bashkirskaya ASSR, Salavat, all of U.S.S.R.

[21] Appl. No.: 593,947

[22] Filed: July 8, 1975

[51] Int. Cl.$^2$ .............................................. C07C 3/62
[52] U.S. Cl. ..................................................... 260/672 T
[58] Field of Search ..................................... 260/672 T

[56] References Cited
U.S. PATENT DOCUMENTS

| 3,597,491 | 8/1971 | Kovach et al. | 260/672 T |
| 3,679,769 | 7/1972 | Kmecak et al. | 260/672 T |
| 3,780,121 | 12/1973 | Suggitt et al. | 260/672 T |
| 3,784,621 | 1/1974 | Suggitt | 260/672 T |

Primary Examiner—C. Davis

Attorney, Agent, or Firm—Fleit & Jacobson

[57] ABSTRACT

A method of preparing benzene and methylbenzenes which comprises heat-treatment of toluene at a temperature of from 350° to 500° C under 1 to 50 atm pressure in the presence of a granulated zeolite catalyst. The latter contains cations of metals of Group II of the periodic system with an exchange degree of 5-30% of the theoretical; hydrogen group with an exchange degree of 6-22% of the theoretical and at least one of two components: the former - cations of metals of Group III of the periodic system with an exchange degree of 20-80% of the theoretical, the latter - cations of transition metals of Period IV of the periodic system with an exchange degree of 24 to 73% of the theoretical. This heat-treatment results in a reaction mixture I containing benzene and xylenes, wherefrom benzene and xylenes are separated. The separated xylenes are heat-treated under the above-mentioned conditions to form a reaction mixture 2 containing toluene and trimethylbenzenes. Toluene and trimethylbenzenes are separated from the reaction mixture 2 and trimethylbenzenes are heat-treated under the above-mentioned conditions to form a reaction mixture 3 containing xylenes and tetramethylbenzenes which are then separated from said mixture.

In this method a total conversion of the starting hydrocarbons to disproportionation products is 40 to 55% which corresponds to 70-95% of the equilibrium.

6 Claims, No Drawings

METHOD OF PREPARING BENZENE AND METHYLBENZENES

The present invention relates to methods of preparing benzene and methylbenzenes such as xylenes (ortho-, para- and meta- isomers), trimethylbenzenes (pseudocumene and mesitylene), tetramethylbenzenes (durol).

These products comprise valuable starting materials for the production of various plastics including water-soluble and heat-resistant ones.

Known in the art production of benzene is based on demethylation of toluene. The process is conducted under rather severe conditions and requires an increased hydrogen consumption. Production of pseudocumene and durol is based on methylation of toluene and xylenes. The process requires an increased consumption of methylating agent and contemplates the use of a catalyst of the aluminium chloride type which, however, contributes to the equipment corrosion.

Also known in the art is a method of preparing benzene and methylbenzenes which does not require the use of hydrogen and methylation agents. The method comprises heat-treatment of toluene at a temperature within the range of from 400° to 500° C under a pressure of from 1 to 50 atm in the presence of a granulated zeolite catalyst of the CaY type with the exchange ratio for calcium of 75 to 80% of the theoretical value. After such a treatment a reaction mixture containing benzene and xylenes is formed. The resulting mixture is subjected to rectification to separate benzene and xylenes. Xylenes are subjected to a further heat-treatment under the above-described conditions. As a result, a reaction mixture is obtained containing toluene and trimethylbenzenes which are recovered, for example, by way of rectification. Toluene isolated from the reaction mixture is recycled to the stage of toluene heat-treatment, while trimethylbenzenes are subjected to a further treatment under the above-described conditions. As a result of such heat-treatment of trimethylbenzenes a reaction mixture is obtained containing xylenes and tetramethylbenzenes which are also recovered from the resulting mixture. The isolated xylenes are delivered to the xylene treatment stage. Durol is isolated from tetramethylbenzenes by crystallization.

In this prior art method, conversion of hydrocarbons to the desired products per one pass, for example at a temperature within the range of from 400° to 450° C, pressure 15 to 40 atm and a space velocity of 1–1.5 hr$^{-1}$ is only 40%. This may be attributed to the fact that said catalyst employed in the process has but a relatively low activity and, which is most important, features an insufficient stability of its action. Thus, when continuously used at a temperature of over 450° C for 50 hours, its activity is reduced by two times or even more. Repeated oxidizing regeneration of the catalyst results in an irreversible loss of activity (ageing). This makes the technological process scheme rather complicated, whereby annual output of the plant becomes substantially decreased and the catalyst consumption is increased to a considerable extent.

It is an object of the present invention to provide such a method of producing benzene and methylbenzenes which would make it possible to produce the desired products at a higher process output and using a simplified process scheme.

This and other objects of the present invention are accomplished by a method of producing benzene and methylbenzenes which comprises heat-treatment of toluene at a temperature ranging from 350° to 500° C and under a pressure within the range of from 1 to 50 atm in the presence of a granulated zeolite catalyst containing cations of metals of Group II of the periodic system with an exchange degree of from 5 to 30% of the theoretical value, a hydrogen group with an exchange degree of from 6 to 22% of the theoretical and at least one of two components: the former representing cations of metals of Group III of the periodic system with an exchange degree of from 20 to 80% of the theoretical value, and the latter representating cations of transition metals of Period IV of the periodic system with an exchange degree of from 24 to 73% of the theoretical value to form a reaction mixture I containing benzene and xylenes, followed by isolation, from said reaction mixture I, of benzene and xylenes, the latter being subjected to a heat-treatment under the above-mentioned conditions to form a reaction mixture 2 containing toluene and trimethylbenzenes, folowed by isolation of toluene and trimethylbenzenes therefrom; said trimethylbenzenes being subjected to a further heat-treatment under the same conditions to form a reaction mixture 3 containing xylenes and tetramethylbenzenes, followed by separation, from said reaction mixture 3, of xylenes and tetramethylbenzenes.

The aforesaid cationic composition ensures a high activity of the catalyst during the disproportioning of methylbenzenes. The presence of cations of metals of Group II of the periodic system hinders migration of cations of metals of Group III and cations of transition metals of Period Iv of the periodic system to inaccessible, for the reagents, spots of the crystal lattice of the zeolite, thus reducing "ageing" of the catalyst and prolonging its life time.

In order to increase the annular process output and to reduce the catalyst consumption rate, it is advisable to perform the heat-treatment of toluene, xylenes and trimethylbenzenes in a medium of an inert gas such as nitrogen or hydrogen at a molar ratio between toluene or methylbenzene to said gas equal to 1:1–10 respectively. Such embodiment of the heat-treatment results in a substantially lesser coke-deposition on the catalyst, whereby the time of its stable operation is substantially increased.

In order to employ xylenes to a maximal possible extent from the xylenes recovered from the reaction mixture I, metaxylene is recovered by way of rectification and subjected to a heat-treatment at a temperature within the range of from 350° to 500° C under a pressure within the range of from 1 to 50 atm in the presence of a granulated zeolite catalyst containing cations of metals of Group II of the periodic system with an exchange degree of from 5 to 30% of the theoretical, a hydrogen group with an exchange degree of from 6 to 22% of the theoretical and at least one of two components: the former representing cations of metals of Group III of the periodic system with an exchange degree of from 20 to 80% of the theoretical, the latter representing cations of transition metals of Period IV of the periodic system with an exchange degree of from 24 to 73% of the theoretical value with the formation of a reaction mixture containing trimethylbenzenes.

Due to the use of the catalyst according to the present invention, in these processes a total conversion of the starting hydrocarbons to the disproportionation products is 40 to 55% which corresponds to 70–95% of the respective value at equilibrium Continuous all-day tests of the catalyst under the conditions close to commercial ones have shown that after a 1,000 hr run (for each fraction) no noticeable drop of the catalyst activity was observed. Overall operation time of the catalyst without discharging from the reactor was over one year almost at the original activity value without any loss thereof whatsoever. As a consequence, there was no necessity in frequent charging and discharging of the catalyst, oxidizing regenerations, handling operations connected with the supply and removal of the reagents, start-up period, and the like. Furthermore, the catalyst consumption rate was substantially decreased due to the lack of "ageing" and mechanical crushing.

The process is technologically simple and may be performed in the following manner.

Toluene is subjected to a heat-treatment in a direct-flow reactor at a temperature within the range of from 350° to 500° under a pressure of from 1 to 50 atm in the presence of a granulated zeolite catalyst. This treatment results in a reaction mixture I containing benzene, toluene and xylenes. The latter are recovered from said mixture by conventional methods such as, for example, rectification.

The thus-recovered benzene comprises a commercial product. Toluene is recycled to the stage of toluene heat-treatment, while the recovered xylenes comprising an equilibric mixture of isomers are subjected to a heat-treatment in another direct-flow reactor under the same conditions to give a reaction mixture 2 containing toluene, trimethylbenzenes, and xylenes which are recovered therefrom.

The recovered toluene is recycled to the stage of toluene heat-treatment, xylenes - back to the stage of xylenes heat-treatment, while trimethylbenzenes are subjected to heat-treatment under the same conditions. As a result of this heat-treatment a reaction mixture 3 is formed containing xylenes, trimethylbenzenes and tetramethylbenzenes. These products are delivered by conventional means to separation, and xylenes are fed to the stage of heat-treatment of xylenes; trimethylbenzenes - to the stage of heat-treatment of trimethylbenzenes. From tetramethylbenzenes comprising an equilibric mixture of isomers durol (1,2,4,5-tetramethylbenzene) is recovered by conventional methods such as by, for example, crystallization.

When required, the process scheme may contemplate separating, by conventional methods, from xylenes and trimethylbenzenes such valuable products as ortho- and para- xylenes, pseudocumene, mesitylene. This method also makes it possible to convert into trimethylbenzenes and tetramethylbenzenes such less-valuable products as meta-xylene, ortho-xylene, pseudocumene, mesitylene.

Heat-treatment of toluene, xylenes and trimethylbenzenes should be preferably performed in a medium of an inert gas such as nitrogen or hydrogen at a molar ratio between said component and the gas equal to 1:1–10 respectively. As has been mentioned hereinbefore, heat-treatment in an inert gas medium makes it possible to reduce coke-deposition on the catalyst, whereby its stability of operation becomes substantially increased.

For better understanding of the present invention the following specific Examples are given hereinbelow.

EXAMPLE 1

A granulated catalyst consisting of 70 wt.% of zeolite NaY with a molar ratio $SiO_2:Al_2O_3 = 4.7$ and 30 wt.% of aluminium hydroxide is treated with a 10% aqueous solution of calcium chloride and then washed with water, dried at 120° C and calcined in an air current at 550° C. Thereafter, the catalyst is treated with a mixture of 10% aqueous solutions of chlorides of rare-earth elements and ammonium chloride and subjected to washing, drying and calcination under the above-described conditions. In the thus-prepared catalyst, a degree of exchange for calcium is 5%, for hydrogen group — 10%, for rare-earth elements — 80%.

The resulting catalyst in an amount of 1 liter (0.65 kg) is charged into an adiabatic reactor, through which toluene is passed at a space velocity of $0.5$ hr$^{-1}$. Toluene treatment is effected at a temperature of about 450° C under 15 atm pressure in hydrogen atmosphere. Molar ratio between toluene and hydrogen is 1:5. As a result, a reaction mixture is obtained containing 10 to 35% of benzene and 10–15% of xylenes comprising an equilibric mixture of xylene isomers. Toluene conversion to disproportionation products (mainly benzene and xylenes) after 500 hours of continuous operation of the catalyst is 45 to 55% which corresponds to 77–93% of the theoretical value. The yield of hydrogenation products does not exceed 1%. The resulting mixture is subjected to rectification to give benzene, para-, meta-, and ortho-xylenes.

EXAMPLE 2

Meta-xylene recovered in a manner similar to that described in Example 1 is subjected to a heat-treatment on the same catalyst which is pre-regenerated by way of passing a mixture of nitrogen and air therethrough. A mixture of meta-xylene and hydrogen at a molar ratio therebetween of 1:5 respectively is passed through the reactor at a space velocity of $0.5$ hr$^{-1}$ (in respect of meta-xylene) at the temperature of 400° C under the pressure of 30 atm to give a reaction mixture containing 20–30% of toluene and 15–20% of trimethylbenzenes. Overall conversion of meta-xylene after 700 hours of continuous run of the catalyst is 75–85% (80–95% of that at equilibrium) including 45–55% to disproportionation products (80–90% of the equilibrium). Therewith, 20 to 30% of meta-xylene are isomerized to ortho- and para-xylene. The reaction mixture is subjected to rectification to separate trimethylbenzenes.

EXAMPLE 3

Through a reactor charged with 1 l(0.65 kg) of the catalyst described in Example 1 and having been used continuously for 2,520 hours with toluene (the catalyst is pre-regenerated) there are passed, at the space velocity of $0.5$ hr$^{-1}$, xylenes comprising a mixture of para-xylene-24%, meta-xylene - 53%, ortho-xylene - 23% (prepared by the procedure of Example 1). The xylenes are passed through the reactor at the temperature of 425° C and under 30 atm pressure in hydrogen atmosphere. Molar ratio between xylenes and hydrogen is 1:5.

As a result, a reaction mixture is obtained containing 20 to 27% of toluene and 19–21% of trimethylbenzenes. Conversion of xylenes to the disproportionation products for 1,000 hours of continuous run of the catalyst is 45–55% (75–90% of the equilibrium). The reaction mixture is separated in a rectification column to give toluene, xylenes and trimethylbenzenes.

EXAMPLE 4

Trimethylbenzenes recovered in a manner similar to that described in Example 3 in the form of a mixture containing about 95% of trimethylbenzenes (a mixture of pseudocumene, mesitylene and hemimellitene are passed, at the space velocity of 0.5 hr$^{-1}$ (with respect to trimethylbenzenes) through the catalyst described in Example 1. Prior to the experiment the catalyst has been used continuously for about 4,000 hours with toluene and xylene cuts. The catalyst is pre-regenerated by way of passing a mixture of nitrogen and air therethrough. Heat-treatment of trimethylbenzenes is effected in hydrogen medium at the temperature of 400° C under the pressure of 15 atm. Molar ratio between trimethylbenzenes and hydrogen is 1:5. Conversion of trimethylbenzenes to the disproportionation products during 700 hours of the catalyst operation is 50 to 55%. The reaction mixture contains 18–22% of xylenes and 27–30% of tetramethylbenzenes. The latter contain 8–10% of durol, 15–18% if iso-durol and 3–5% of prenitene. Durol is isolated from tetramethylbenzenes by crystallization.

EXAMPLE 5

The catalyst is prepared in a manner similar to that of Example 1, except that the granulated catalyst is treated with a 8% aqueous solution of calcium chloride and then with a mixture of 5% aqueous solutions of chlorides of rare-earth elements and ammonium chloride. In the resulting catalyst the degree of exchange for calcium is 20%, for rare-earth elements —60%, for hydrogen group — 15%.

The resulting catalyst in the amount of 1 l (0.65 kg) is charged into an adiabatic reactor. A mixture of toluene and hydrogen at the molar ratio therebetween of 1:10 respectively is passed through the reactor at the space velocity of 0.5 hr$^{-1}$ (with respect to toluene) at the temperature of 400° C under the pressure of 50 atm.

Conversion of toluene into the disproportionation products (mainly benzene and xylenes) during 800 hours of continuous operation of the catalyst without regeneration is 40 to 52%. After 800 hours of continuous operation the catalyst is regenerated by passing a mixture of nitrogen and air therethrough. An equilibric mixture of xylenes recovered by rectification is passed through the catalyst at 350° C, all other conditions being the same. Conversion of xylenes to the disproportionation products (mainly toluene and trimethylbenzenes) during 700 hours of continuous operation of the catalyst without regeneration is 41 to 53%. Pseudocumene and mesitylene are isolated from the reaction mixture by conventional methods.

EXAMPLE 6

A granulated catalyst consisting of 70% by weight of NaY zeolite with the molar ratio of $SiO_2:Al_2O_3 = 4.7$ and 30% by weight of aluminium hydroxide is treated with a 10% aqueous solution of ammonium chloride, whereafter it is subjected to washing with water, drying at 120° C and calcination in a current of air at 550° C. The resulting granules of the zeolite (decationized form HY) are treated with a mixture of 10% aqueous solutions of nitrates of rare-earth elements, cadmium, magnesium, nickel and washed, dried and calcined under the above-described conditions. Degree of exchange for rare-earth elements is 20% for magnesium - 20%; for cadmium - 10%; for nickel - 24: and for hydrogen group - 22%.

The resulting catalyst in the amount of 6 g is charged into an isothermal reactor. A mixture of ortho-xylene (orthoxylene is prepared as in Example 1) and nitrogen at the molar ratio therebetween of 1:10 respectively is passed through the reactor at the temperature of 450° C, under the pressure of 3 atm and at the space velocity of 0.5 hr$^{-1}$ with respect to ortho-xylene to give a reaction mixture containing 29.1% of toluene, 4.5% of mesitylene, 13.8% of pseudocumene and 2.0% of hemimellitene. Conversion of ortho-xylene is 76%.

EXAMPLE 7

A calcined catalyst in the decationized form (XY) prepared in a manner similar to that described in Example 6 is treated with a mixture of 5% aqueous solutions of nitrates of calcium, chromium, magnesium, aluminium and subjected to washing, drying at 120° C and calcination in a current of air at 550° C. In the resulting catalyst the degree of exchange for calcium is 18%, chromium - 24%, magnesium - 12%; for aluminium - 34% and for hydrogen group - 16%.

5 g of the thus-prepared catalyst are charged into an isothermal reactor. A mixture of ortho-xylene (the ortho-xylene is prepared as in Example 1) and hydrogen at the molar ratio therebetween of 1:10 respectively is passed through the reactor at the space velocity of 3 hr$^{-1}$ with respect to o-xylene at the temperature of 500° C under 1 atm pressure to give a reaction mixture containing 28.2% of toluene and 16.1% of trimethylbenzenes. Conversion of ortho-xylene is 72.4%. The trimethylbenzene fraction contains 22.1% of mesitylene, 68.2% of pseudocumene and 9.7% of hemimellitene.

EXAMPLE 8

A granulated catalyst in its decationized form prepared as in Example 6 is treated with a mixture of 10% aqueous solutions of chlorides of copper and magnesium and subjected to washing, drying and calcination under the conditions described in the foregoing Example 7. Degree of exchange for calcium is 29%, for copper - 45%, and for hydrogen group - 20%.

30 g of the thus-prepared catalyst are charged into an isothermal reactor. Toluene is passed through the reactor at the space velocity of 0.6 hr$^{-1}$ at the temperature of 450° C under the pressure of 50 atm to give a reaction mixture containing 23.4% of benzene, and 19.6% of xylenes. Conversion of toluene is 48.2%. Xylene fraction contains 24.0% of para-xylene, 53% of meta-xylene and 23% of ortho-xylene.

EXAMPLE 9

A granulated catalyst in its decationized form prepared as in Example 6 is treated with a mixture of 8% aqueous solutions of chlorides of calcium, rare-earth elements and manganese. After washing, drying at 120° C and calcination in a current of air at 550° C, the degree of exchange for calcium is 8%, for rare-earth elements - 54%, for manganese - 26%, and for hydrogen group - 6%.

5 g of the thus-prepared catalyst are charged into an isothermal reactor thorugh which a mixture of pseudocumene (the latter is prepared as in Example 5) and hydrogen at the molar ratio therebetween of 1:10 respectively is passed at the space velocity of 1 hr$^{-1}$ at the temperature of 350° C and under 4 atm pressure to give a reaction mixture containing 20.7% of xylenes and 23.8% of tetramethylbenzenes. The latter fraction has the following composition: durol 35%, isodurol 52%, prenitene 13%. Xylene fraction contains 23.4% of para-xylene, 53.9% of meta-xylene and 22.7% of ortho-xylene.

Pseudocumene conversion is 69.3%.

EXAMPLE 10

A granulated catalyst in its decationized form prepared as in Example 6 is treated with a mixture of aqueous 5% solutions of magnesium, iron, cobalt and zinc chlorides and subjected to washing, drying and calcination under the conditions of Example 1. The degree of exchange for magnesium is 15%, for iron - 22%, for cobalt - 37%, for zinc - 14% and for hydrogen group - 7%.

6 g of the thus - prepared catalyst are charged into an isothermal reactor through which a mixture of meta-xylene (the latter is prepared as in Example 1) and hydrogen is passed at the space velocity of 1 hr$^{-1}$ with respect to meta-xylene at the molar ratio therebetween of 1:2 respectively at the temperature of 400° C under 3 atm pressure to give a reaction mixture containing 25.3% of toluene and 20.6% of trimethylbenzenes. Trimethylbenzene fraction contains 21.4% of mesitylene, 69.1% of pseudocumene, and 9.5% of hemimellitene. Overall conversion of ortho-xylene is 74.1%.

Examples 11 through 15 are summarized in the tables following hereafter. Thermal treatment is effected using a catalyst similar to that described in Example 1.

| Example No. | Catalyst charge, g | Treated product | Space velocity, hr$^{-1}$ | Temperature, °C | Pressure, atm | Component content in the reaction mixture, wt. % | Conversion, % |
|---|---|---|---|---|---|---|---|
| 11 | 30 | toluene | 0.6 | 500 | 15 | benzene 18.5 xylenes 20.5 | 43.7 |
| 12 | 40 | meta-xylene | 0.6 | 425 | 15 | toluene 17.4 trimethyl-benzenes 22.7 | 64.4 |
| 13 | 30 | pseudocumene | 0.6 | 450 | 50 | xylenes 19.2 tetramethyl-benzenes 29.1 | 65.6 |
| 14 | 650 | xylenes (mixture of para-xylene 24%, metaxylene 53%, orthoxylene 23% | 0.5 | 400 | 30 | toluene 14.9 trimethyl-benzenes 18.0 | 45.6 |
| 15 | 50 | toluene:nitrogen = 1:2 (molar ratio) | 1,0 | 450 | 15 | benzene 14.2 xylenes 16.9 | 35.3 |

What is claimed is:

1. A method of preparing benzene and methylbenzenes comprising contacting toluene at a temperature within the range of from 350° to 550° C. under a pressure of from 1 to 50 atmosphers with a granulated zeolite catalyst containing cations of metals of Group II of the periodic system with an exchange degree of from 5 to 30% of the theoretical value, hydrogen group with an exchange degree of from 6 to 22% of the theoretical value, and cations of metals of Group III of the periodic system with an exchange degree of from 20 to 80% of the theoretical value to form a reaction mixture I containing benzene and xylenes, separating benzene and xylenes from said reaction mixture I; contacting the separated xylenes with the same catalyst under the same conditions described above to form a reaction mixture II containing toluene and trimethylbenzenes, separating said toluene and trimethyl-benzenes from said reaction mixture II; contacting the separated trimethylbenzenes with the same catalyst under the same conditions described above to form a reaction mixture III containing xylenes and tetramethylbenzenes, and separating said xylenes and tetramethylbenzenes.

2. A method as claimed in claim 1, wherein said contacting of toluene is effected in an inert gas medium selected from the group consisting of hydrogen and nitrogen at a molar ratio between toluene and the inert gas equal to 1:1-10.

3. A method as claimed in claim 1, wherein said contacting of xylenes is effected in a medium of an inert gas selected from the group consisting of hydrogen and nitrogen at a molar ratio between xylenes and the inert gas equal to 1:1-10.

4. A method as claimed in claim 1, wherein said contacting of trimethylbenzenes is effected in a medium of an inert gas selected from the group consisting of hydrogen and nitrogen at a molar ratio between trimethylbenzenes and the inert gas equal to 1:1-10.

5. A method as claimed in claim 1, wherein, from the xylenes separated from reaction mixture I, meta-xylene is separated by rectification and contacted at a temperature within the range of from 350° to 500° C. under a pressure of from 1 to 50 atmospheres with a granulated zeolite catalyst containing cations of metals of Group II of the periodic system with an exchange degree of from 5 to 30% of the theoretical value, hydrogen group with an exchange degree of from 6 to 22% of the theoretical value, and cations of metals of Group III of the periodic system with an exchange degree of from 20 to 80% of the theoretical value with the formation of a reaction mixture containing trimethylbenzenes.

6. A continuous method of preparing benzene and methylbenzenes which comprises:

a. contacting toluene at a temperature of about from 350° C. to 500° C. under 1 to 50 atmospheres pressure with a granulated zeolite catalyst containing cations of metals of Group II of the periodic system with an exchange degree of about from 5% to 30% of the theoretical value, hydrogen group with an exchange degree of about from 6% to 22% of the theoretical value, and cations of metals of Group III of the periodic system with an exchange degree of about from 20% to 80% of the theoretical value, said contacting of the toluene being conducted in the presence of an inert gas selected from the group consisting of hydrogen and nitrogen in which the toluene and inert gas are present in the molar ratio of about 1:1-10, respectively, to form a reaction mixture I containing toluene, benzene, and xylenes consisting of the ortho-, meta- and para-isomers;

b. separating the benzene, toluene and xylenes from each other, recovering the benzene, and recycling the toluene back to step (a) for further processing;

c. contacting the xylenes from step (b) with the same catalyst under the same conditions as in step (a), with the xylenes and inert gas being present in the same molar ratio of about from 1:1-10, respectively, to form a reaction mixture II containing toluene, xylenes, and trimethylbenzenes;

d. separating the toluene, xylenes, and trimethylbenzenes from each other, recycling the toluene back to step (a) and recycling the xylenes back to step (c) for further processing;

e. contacting the trimethylbenzenes from step (d) with the same catalyst under the same conditions as in step (a), with the trimethylbenzenes and inert gas being present in the same molar ratio of about from 1:1-10, respectively, to form a reaction mixture III containing xylenes, trimethylbenzenes, and tetramethylbenzenes;

f. separating the xylenes, trimethylbenzenes, and tetramethylbenzenes from each other, recycling the xylenes back to step (c) and recycling the trimethylbenzenes back to step (e) for further processing, and recovering the tetramethylbenzenes.

* * * * *